US008688471B2

(12) United States Patent
Chien

(10) Patent No.: US 8,688,471 B2
(45) Date of Patent: Apr. 1, 2014

(54) SYSTEM, APPARATUSES AND METHODS TO INCREASE SUPPLY OF SPECIALTY CARE SURGICAL-MEDICAL TREATMENTS

(75) Inventor: Cl. Alex. Chien, Haslett, MI (US)

(73) Assignee: HCM-Info, LLC., Suttons Bay, MI (US)

( * ) Notice: Subject to any disclaimer, the term of this patent is extended or adjusted under 35 U.S.C. 154(b) by 175 days.

(21) Appl. No.: 13/229,622

(22) Filed: Nov. 3, 2011

(65) Prior Publication Data

US 2012/0330673 A1 Dec. 27, 2012

Related U.S. Application Data

(63) Continuation-in-part of application No. 12/255,711, filed on Oct. 22, 2008, now abandoned.

(60) Provisional application No. 61/000,868, filed on Oct. 30, 2007, provisional application No. 61/125,721, filed on Apr. 30, 2008.

(51) Int. Cl.
*G06Q 50/00* (2012.01)
(52) U.S. Cl.
USPC .......................................................... 705/2
(58) Field of Classification Search
USPC ........................................................ 705/2, 3
See application file for complete search history.

(56) References Cited

U.S. PATENT DOCUMENTS

2003/0028400 A1* 2/2003 Christ et al. ...................... 705/2
2010/0030579 A1* 2/2010 Dhauvan ........................... 705/3

OTHER PUBLICATIONS

Indian Health Services website (http://www.ihs.gov) "Find Health Care" —North Dakota.*
Blue Cross & Blue Shield website (http://www.bcbsms.com) "Ambulance and medical Transport Service" Policy; Feb. 1998.*

* cited by examiner

*Primary Examiner* — John Pauls

(57) ABSTRACT

System, apparatuses and methods for treating specialty care surgical-medical patients (10) who are medically-stable. A specialty care surgical-medical hospital-clinic (40) is sited on a quasi-sovereign geographic area, including federally-recognized American Indian/Alaskan Native tribal nations. Surgical-medical treatments by provider group (42) who are citizens of countries worldwide. Transportation (30) of patients to hospital-clinic (40) by non-emergency vehicles. Treatment of patients (10) maximized via surgical-medical expertise from other hospital-clinics (60) provided via information technology systems (50) connected by global wide-area network linkages (62).

1 Claim, 2 Drawing Sheets

Figure 1:
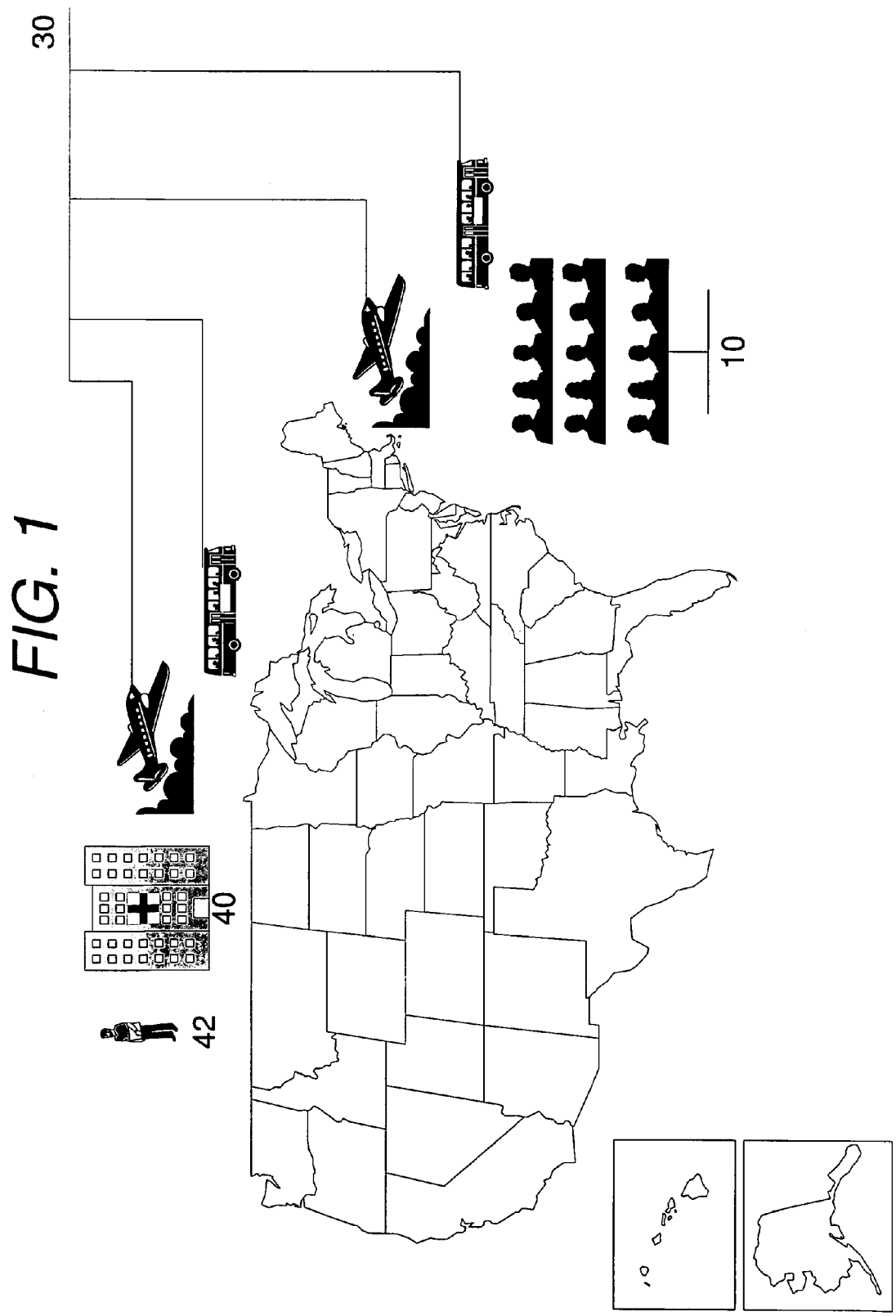

SYSTEM, APPARATUSES AND METHODS TO INCREASE SUPPLY OF SPECIALTY CARE SURGICAL-MEDICAL TREATMENTS

CROSS-REFERENCE TO RELATED APPLICATIONS

This continuation-in-part application claims the benefit of provisional application Ser. No. 61/000,868 filed on Oct. 30, 2007 (acknowledgment mailed Dec. 27, 2007) and Ser. No. 61/125,721 filed on Apr. 30, 2008, both by Applicant. Also continuation-in-part of application Ser. No. 12/255,711, filed on Oct. 22, 2008, now abandoned and which is incorporated herein by reference.

FEDERALLY SPONSORED RESEARCH

Not Applicable

SEQUENCE LISTING OR PROGRAM

Not Applicable

BACKGROUND OF THE INVENTION

1. Field of the Invention

This invention generally applies to delivering specialty care surgical-medical treatments to patients who are medically-stable.

2. Prior Art

In 2008, the health care system in the United States was troubling for patients, taxpayers and the public. It was described by one observer as "dysfunctional . . . broken." With "patient needs" frequently "clashing with economic reality" to produce "staggering" waste. A significant part of health care costs are for specialty care surgical-medical treatment, including cardiac care.

Concurrently, the well-being of the more than 520 federally-recognized sovereign American Indian/Alaskan Native (AI/AN) tribal nations was very uneven. First, after decades of strong efforts—starting in small meeting halls—some tribal nations near resort areas and metro areas built on their federally-recognized sovereignty. They offered constitutionally-authorized gaming and prospered.

Typically, large American Indian/Alaskan Native (AI/AN) gaming facilities were managed and/or supported by outside gaming-management firms from across the world; tribal nations retained executive oversight. This was similar to university-affiliated hospital management groups (e.g., Harvard, Johns Hopkins, Duke) providing expertise to establish state-of-the-art health care facilities in the Middle East and Asia.

However, most AI/AN tribal nations still struggled mightily with serious issues, such as lack of Rural American jobs, economic development, economics, health care, the lingering effects of decades of brutal, ugly racism, and what AI/AN leaders believed as institutional indifference to AI/ANs. Mostly located in Rural America, these tribal nations regularly testified before Congress about what they charged were inappropriate levels of funding that had been made under treaties, the U.S. Constitution and other agreements. Also, a Harvard-affiliated study in 2009 asserted that, despite promises by U.S. leaders to "Indian Country," American Indian/Alaskan Native tribal nations lacked appropriate access to specialty care surgical-medicine.[1]

[1] http://www.nativetimes.com/index.php?option=com_content&view=article&id=4723:study-ihs-lacks-accessibility-to-specialty-care-other-resources&catid=48&Itemid=24

As to American Indian/Alaskan Native economic development, one metric: in 2008 there were three (3) patents and one (1) patent application directly involving the AI/AN community in the USPTO database, from a base of millions of filings. None involved medical care. Those four citations are at the front of this application.

Indian Health Service (IHS)—A Federal Agency Only for American Indians/Alaskan Natives As to adequate health care for AI/AN tribal nations: by the U.S. Constitution, treaties, court rulings and agreements dating back before the 1776 founding of the U.S., the U.S. government had agreed to provide members of federally-recognized AI/AN tribal nations with public services, including health care, at no cost. Today, the Indian Health Service (IHS) of the U.S. is the responsible federal agency, assigned to care for enrolled members (and families) of federally-recognized American Indian/Alaskan Native tribal nations.

However, given IHS funding levels, many tribal nations strongly questioned whether those commitments were being honored appropriately. Those tribal nations demanded that the U.S. government fulfill what the tribal nations believe were negotiated obligations. Further, Congress regularly held investigative hearings on how appropriately the federal government was meeting performance standards. And a 2009 Harvard-affiliated study cited a substantial lack of specialty care surgical-medicine in Indian Country.

With its legally-mandated mission to deliver health care only to enrolled members of federally-recognized American Indian/Alaskan Native tribal nations, the federal Indian Health Service operates or funds tribal-nation health clinics and community-sized tribal-nation hospitals (>75 beds). IHS can directly provide primary, emergency, outpatient, and maternity care for American Indians/Alaskan Natives; it can also contract-out for other services at larger hospitals that are geographically distant from IHS clinics in Rural America. IHS can also directly provide general medical services to American Indians/Alaskan Natives who live in urban centers (e.g., Phoenix, Portland, Oreg.).

Approximately 0.57% (less than 1.00%) of IHS patient visits in 2007 required overnight hospitalization. Many IHS clinics are in very sparsely-populated rural areas; note following on Alaskan Natives.

U.S. Health Care System: Severely-Challenged

As to the oft-troubled U.S. health care system: the U.S. was not unique in that conundrum. Health care systems of the world's nations chronically had operational and financial problems. Those problems included funding, level and quality of treatment, organizational structuring, and quarrelsome labor relations (including provider strikes). As a result, many countries reported significant financial strain.

In the U.S., among the long-standing and systemic issues in medical care cited by the U.S. news media:
- medical costs rising higher than general inflation, unaffordability;
- few, if any, patient options on provider choice;
- uneven service-levels, with over-serviced metros and under-serviced rural areas reported;
- very high level of bureaucracy and organizational conflict, including seemingly-perpetual litigation;
- uneven quality, including in single-payer programs such as Veterans Administration; and
- higher costs that can accompany large numbers of small, dispersed providers.

Many patients in a wide variety of medical-insurance plans described the situation in U.S. medical-care as personally difficult. That is, dealing personally with coverage questions and costly, highly-stressful billing disputes with providers, payers, and state and federal agencies, including Medicaid and Medicare.

Further, in Medicaid and Medicare, increasing numbers of treatment-providers were withdrawing from those programs, citing acrimoniously-debated provider-reimbursement levels.

Also, many asserted that a significant barrier to lowering medical costs were substantial regulatory and legal issues. Example: some asserted that because U.S. specialty care surgical-medical groups can strongly influence the supply of new providers, such groups can strongly influence pricing, staffing, and other issues.

As noted, a major part of a nation's health care costs are specialty care surgical-medical treatments. Such treatments have been defined by voluntary associations of medical-surgeons and dental-surgeons as colon and rectal, vascular, surgery of the hand, neurologic, ophthalmologic, oral and maxillofacial, orthopaedic, otolaryngology, plastic surgery, thoracic and cardiovascular, and urologic.

Further, because any proposed change to U.S. provider-practices can require reviews by many groups—e.g., American Medical Association (AMA), Medicare, Medicaid, American Hospital Association (AHA)—attempts to make cost-containment changes can take a very long time.

Also, in the opinion of many, the possibility of questionable medical-malpractice lawsuits were increasing costs. Example: wide-spread usage of marginally-useful but costly medical testing, ostensibly to deter lawsuits. Among the outcomes cited: increased costs, costly and wasteful "defensive medicine," and deterred investment in provider-practice innovation. Indeed, to keep charity clinics operating, some states restricted the filing of medical-malpractice lawsuits against such clinics.

"Medical Tourism" & the USA

As a result of the aforementioned, growing numbers of U.S. residents in the mid-2000s began traveling to countries such as India, Hungary and Thailand for more affordable medical care. That included treatment in specialty care surgical-medical practice areas such as cardiovascular. This was popularly known as "medical tourism."

It was widely reported by the U.S. news media that "medical tourism" treatments outside the U.S. could cost up to 80% less than in the U.S. That could reduce direct costs by as much as $300,000 per treatment. Uninsured Americans were reported by the news media as very interested in that significant price differential. One case involved a U.S. citizen who flew to India for a heart transplant.[1]

[1] http://seattletimes.nwsource.com/html/nationworld/2013051960_indiatransplant03.html However, not all "medical tourism" clinics were accredited via global agencies such as Joint Commission International (JCI), as most U.S. hospitals are. Conversely, a few "medical tourism" hospitals in Asia drew praise from outside experts for their highly-focused treatment processes.

In any event, the much-lower cost of "medical tourism" enabled payment on an upfront cash basis. Later, patients would seek reimbursement from their U.S. payers, including Blue Cross/Blue Shield, employer plans, and private insurers.

A significant factor behind the cost differential between the U.S. and "medical tourism" countries: costs outside the U.S. for providers such as medical doctors were typically lower.[2] Even though many overseas providers had been trained in USA-level United Kingdom facilities and some in the U.S. and USA-affiliated facilities.

[2] http://www.nytimes.com/2011/09/08/us/08docs.html?_r=1&ref=health

Many Attempts, Many Failures

In response to these obviously-distressing situations, inventors attempted to devise solutions, mostly piecemeal. A search of USPTO 705/2 class of health care management revealed patents mostly about health information technology—not hands-on, multi-functional aspects of clinical treatment of patients.

Public figures also commented (e.g., "ObamaCare," immediate legal challenges to "ObamaCare"). In over-arching generalities, some wrote about the need for global professional staffing. Others offered theoretical strategies for total U.S. system overhauls—which, given the large number of politically-powerful, moneyed factions involved, would be challenging.

In more practically-oriented commentary, Prof. Regina Herzlinger of Harvard championed U.S. medical doctors opening new medical clinics focused on a few procedures (e.g., hip replacements) to gain cost-efficiencies. J. Hwang. MD/MBA. and Prof. Clayton Christensen, DBA, both of Harvard, identified regulatory issues as blocking U.S. health care innovation—but offered no specific solutions publicly.

Alaskan Tribal Nations Assert Sovereignty in Health Care

On Monday, Apr. 28, 2008, atop its front page, "*The New York Times*" focused attention on the emergence of a new, basic-level medical care/health care provider. From the Alaskan tribal nations' remote Arctic-lands—the dental therapist (DT).

For at least four years, the DT practice issue had been quietly simmering. The DT's role was similar to that of a physician's assistant—limited, non-surgical practice under supervision of a state-licensed practitioner—but rarely used in the U.S. for reasons unknown.

Near-desperate for basic dental services in their remote Arctic homelands, after decades of very limited recruiting success, the Alaskan Native tribal nations decided to directly contract with New Zealand colleges to import DTs. And to begin DT-training programs for Alaska's bitterly-cold Arctic.

In response, the American Dental Association (ADA), the largest group of DDS-practitioners, sued the Alaskan Native tribal nations. ADA alleged that the tribal nations were practicing dentistry without a license.

After Alaskan Native tribal nations won the first state court hearing, ADA stopped litigating, paid the tribal nations' legal fees, and agreed to work cooperatively.

Federally-Recognized Sovereignty of American Indian/Alaskan Native Tribal Nations To most tribal nations, the ADA-Alaska Native matter was just another replay of a very frequent, expensive, and litigation-intense occurrence—either (1) lack of understanding of federally-recognized tribal-nation sovereignty, (2) lack of respect for federally-recognized tribal-sovereignty, or (3) some combination thereof. Privately, American Indian/Alaskan Native leaders wondered how much of the issue was related the lingering traces of brutal, ugly racism toward Native Peoples.

The sovereign status of federally-recognized American Indian/Alaskan Native tribal nations with the U.S. is at the core of the present invention. Federally-recognized American Indian/Alaskan Native tribal nations assert that by the U.S. Constitution, various agreements (some signed before 1776) and the U.S. Supreme Court's *Cabazon* ruling, they have certain sovereign rights of national self-determination.

Those federally-recognized sovereign rights include self-determination on what are appropriate tribal-nation activities. Those sovereign activities include tribal-nation law-making, tribal courts, tribal public safety, gaming and other enterprises, cigarette sales, vehicle registration and public services.

The *Cabazon* decision affirmed the federally-recognized sovereign right of the *Cabazon* tribal nation and other federally-recognized American Indian/Alaskan Native tribal-nations to offer high-stakes bingo and gaming, pre-empting state law. *Cabazon* serves as the legal foundation of the national AI/AN gaming industry and other sovereign tribal-nation activities.

Thus, based on *Cabazon* and the Alaskan DT matter, as well as experience, information and belief, the present invention in the illustrated embodiment assumes: federally-recognized tribal-nation sovereignty includes tribal authority related to the appropriate delivery of specialty care surgical-medical services on quasi-sovereign tribal property. Also included: related support services.

Further, that federally-recognized quasi-sovereign authority includes jurisdiction over allegations of medical malpractice. That litigation is significant component of medical-care costs in the U.S. On allegations of medical malpractice, that AI/AN sovereignty can include: mandatory arbitration for allegations of medical malpractice; establishing a reserve fund to appropriately compensate those injured in the rare, inevitable medical errors; and setting an appropriate award-cap on debatable "pain-and-suffering" claims. As noted, some states have approved such regulations to restrain medical-malpractice costs from bankrupting charity clinics.

"Telemedicine" & Rural America

Now, "Fortune 500" companies and academics have claimed for decades that "telemedicine" would improve the lives of patients. Telemedicine—which does not involve direct, hands-on clinical treatment of patients—is defined as "the use of medical information exchanged from one site to another via electronic communications." Telemedicine includes physician-to-physician consultations, patient consultations, and remote patient monitoring. It is also known as "telehealth," "telepsychology," "telepharmacy" and "telecardiograms."

Telemedicine dates back to the first NASA Mercury human space flights of the late 1950s. Then, vital signs of astronauts were relayed to NASA ground stations via telemetry. Telemedicine is well-known, such as U.S. Pat. No. 6,820,057 to Loch, et al. (proprietary telemetry protocol), and U.S. Pat. No. 7,912,733 to Clements, et al. (Texas prison health care via telemedicine).

In 1994, the first experiment with telemedicine and a tribal nation began, from rural South Dakota. Tribal members were visually "examined" by Mayo Clinic physicians via video cameras and satellite video-links. More recently, tribal nations in remote areas of the Western USA used "telepsychology" and "telehealth" to provide intra-state mental health and basic health examinations.

In the illustrated embodiment of the present invention, the state of North Dakota has a statewide public fiber-optic network. Thus, many applications of wide-band video-telemedicine can be supported.

However, many American Indians/Alaskan Natives live in rural areas without fiber-optic networking. As such, for the high-speed inter-networking required for video "telemedicine," satellite links that are occasionally problematic (e.g., signal-interference during heavy precipitation) would be required. Also, satellite networks can be used for system-redundancy, as a back-up network pathway.

3. Objects and Advantages

The purpose of my invention is to improve on prior art, to provide a citizenry highly-stressed about affordable medical care with another choice for high-quality specialty care surgical-medical treatment. New surgical-medical facilities, strong sovereign leadership, collaborative relationships worldwide, high-quality global provider teams, and cost-effective global support for quality via information technology/com-puting/communications accomplish that goal. My invention results from more than 25 years of front-line, hands-on experiences in technology, medical care, health care, and working collaboratively with Native Peoples—a novel, nonobvious creation from existing components. And that holds the promise of more reliable surgical-medical treatment delivery. Among the objects and advantages:

1. to give persons in medically-stable condition another treatment option, rather than flying up to 16,000 miles to exotic locations. For affordable surgical-medical treatment and eliminate the accompanying carbon-emission issues.
    a. Given the reduced need for travel, there is an obvious much-greater likelihood that a patient can be accompanied to treatment by loved ones.
    b. The treatment environment will be safer and more secure, with rule of law paramount.
    c. Per previous, retain those expenditures within the local economy.
2. to provide, with the support of computer-implemented global wide-area networking and cost-effective global staffing, many benefits:
    a. rapidly-accelerated development for American Indian/Alaskan Native tribal nations, accomplished in years rather than decades;
    b. committed high level of treatment quality for patients, dedicated capability for handling most specialty care surgical-outcomes via cost-effective support from global affiliates; and
    c. create new knowledge for the world, in a cost-effective manner.
3. to create jobs and economic development for American Indian/Alaskan Native tribal nations and Rural America, who have testified to Congress that they have been neglected for decades.
    a. increase meaningful and positive collaboration between AI/AN tribal nations, U.S. government, state and local governments, overseas nations and others.
4. to motivate existing providers to meet new, higher standards of service.
5. to provide another solution to the Medicaid/Medicare funding dilemma.
6. to "add new voices" to the best-practices examination of global medical care.
7. to create the very rare: a "clean-sheet/green-field/blue-ocean" opportunity to implement "best practices" in specialty care surgical-medical practice. Without repeated interference from, as noted previously, deeply-entrenched organizations that are well-funded and self-interested in preserving the status quo.
8. to provide the federal Indian Health Service with another choice of vendor for specialty care surgical-medical treatments. To be clear:
    a. Specialty care surgical-medical hospital-clinic 40 is 100%-separate from any IHS facility. Hospital-clinic 40 is offering specialty care surgical-medical treatments. As such, hospital-clinic 40 is complementary rather than duplicative of IHS health services.
    b. More specifically, per Applicant's art, specialty care surgical-medical hospital-clinic 40 is available to groups of non-American Indian/Alaskan Native patients 10, who are medically-stable and have scheduled examinations and treatments. While the mission of the oft-scrutinized federal Indian Health Service is to treat only American Indians/Alaskan Natives, including emergency services.

Further objects and advantages will become apparent from the ensuing description and drawings.

SUMMARY

In accordance with the present invention—system, apparatuses and methods to treat specialty care surgical-medical patients in medically-stable condition, comprising a hospital-clinic on a quasi-sovereign geographic area, including tribal nations, by a provider group from across the world, and computer-linked to affiliates worldwide for maximal treatment quality.

DRAWINGS

Figures

Figure 2:
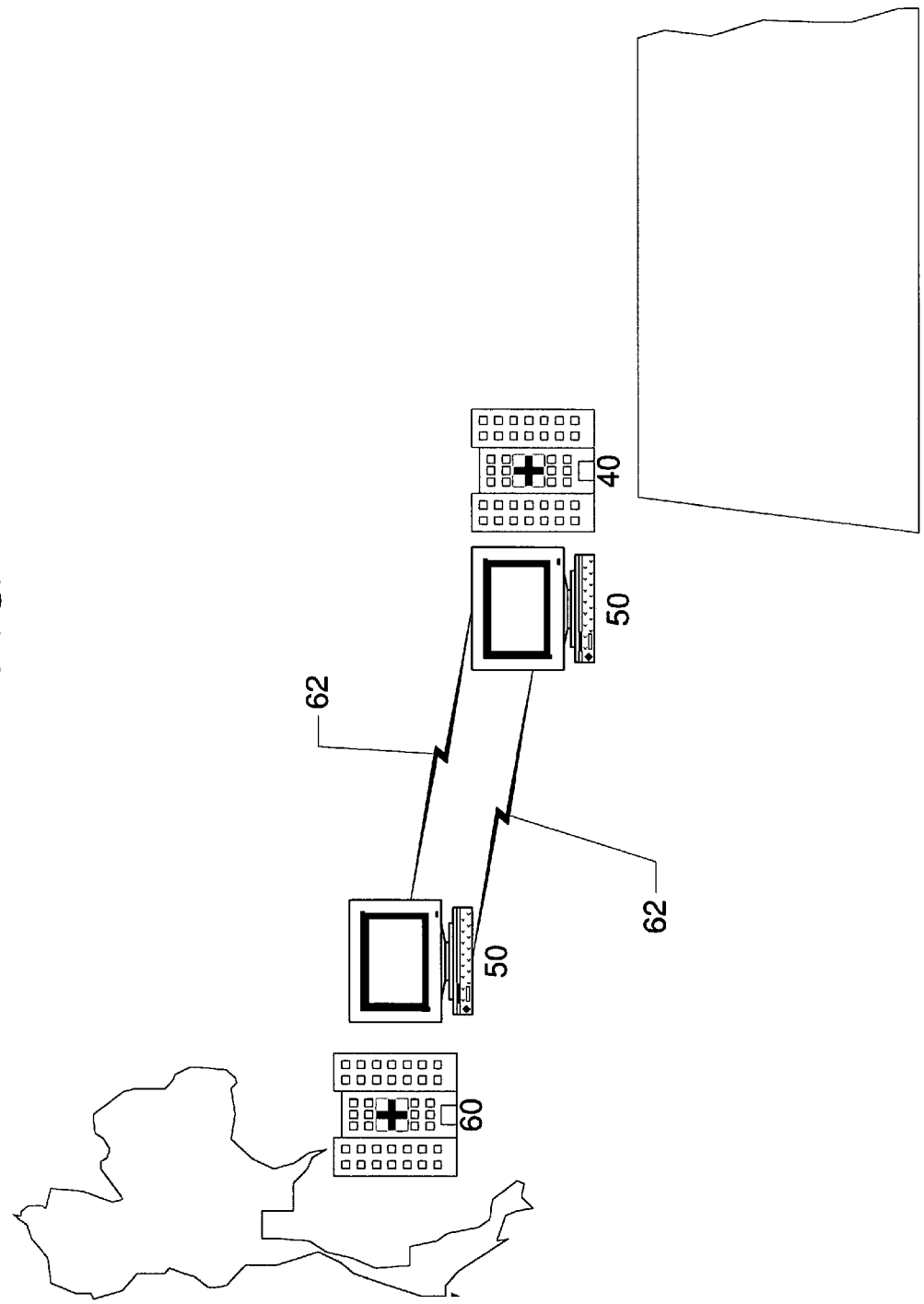

FIG. 1—System view—a simplified illustration showing my invention in an illustrated embodiment; and FIG. 2—Wide-area network of a global nature—a simplified drawing illustrating my invention's information-technology systems 50 for communications and computing and wide-area network linkages 62. Which enable consultations to ensure maximal patient treatment quality, as well as hospital-clinic operations.

REFERENCE NUMERALS 10 patients (medically-stable, non-emergency, ambulatory)
30 patient transport (illustrated: airplane & bus; non-emergency)
40 hospital-clinic on quasi-sovereign area, including tribal nations
42 specialty-care surgical-medical group (e.g., providers, administrators)
50 information technology systems (for communications and computing)
60 affiliated hospital-clinic for maximal patient care support
62 wide-area network linkage(s)

DETAILED DESCRIPTION & OPERATION

FIGS. 1 AND 2—Illustrated Embodiment

An illustrated embodiment of my invention is presented in FIG. 1 (Mandan, North Dakota USA view) and FIG. 2 (global view), enabling a system-wide review. It is understood that other embodiments may be utilized; structural and operational changes may be made without departing from the scope of the invention.

In this illustrated embodiment, per U.S. government agreements on American Indian/Alaskan Native sovereignty, in FIG. 1, a specialty care surgical-medical hospital-clinic 40 separate from the federal Indian Health Service (IHS) has been established on a quasi-sovereign, federally-recognized tribal nationland in Mandan, North Dakota. Surgical-medical hospital-clinic 40 was established after the federally-recognized sovereign tribal nation, U.S. government and others agreed to work collaboratively to give patients another treatment choice. Hospital-clinic 40 was constructed under the supervision of surgical-medical group 42 and the tribal nation, as Harvard University affiliates have in developing health care facilities in the Middle East. In this embodiment, the tribal nation has also decided that surgical-medical hospital-clinic 40 and provider group 42 should be accredited by third-party accrediting agencies, rather than by the quasi-sovereign tribal nation. Clinic can be either of fixed-base construction or mobile units.

In this embodiment, the tribal nation is within 120 miles of an airfield capable of handling 150-passenger jet-airplanes, for transport of up to 150 medically-stable and ambulatory patients 10 (who may not or may be American Indians/Alaskan Natives) to nearby surgical-medical hospital-clinic 40. (Federal law is specifically clear that non-American Indians/Alaskan Natives are not eligible for Indian Health Service patient care.) As clearly illustrated in FIG. 1, to and from the airfields, transport 30 of patients 10 involves passenger buses that are not emergency vehicles (i.e., ambulances). Also, as clearly illustrated by FIG. 2, the aircraft involved is not an emergency vehicle (i.e., air ambulance).

In FIG. 1, after surgical-medical hospital-clinic 40 has been established, appointments for medically-stable patients 10 are set by specialty-care surgical-medical provider group 42. As with "medical tourism," medically-stable patients 10 (who may not or may be American Indians/Alaskan Natives) have contacted hospital-clinic 40 and provider group 42 in a variety of ways—such as personal initiative in calling a toll-free number, provider referral, referral by insurance plan, or via the World Wide Web.

After appointments are confirmed to medically-stable and ambulatory patients 10, patients 10 gather at a scheduled time to be transported 30 by non-emergency passenger bus(es) and airplane(s) to surgical-medical hospital-clinic 40. Immediately prior to the arrival of patients 10, administrators and allied staff of provider group 42 have scheduled, staffed and provisioned hospital-clinic 40 to the highest clinical standards required under accreditation guidelines, in this embodiment.

Once at hospital-clinic 40, medically-stable patients 10 are admitted and appropriately treated by specialty-care surgical-medical providers from surgical-medical group 42. This is similar to "medical tourism"—except the patients have not flown up to 8,000 miles by carbon-emitting jet aircraft.

In FIG. 2, during the stay of medically-stable patients 10 at surgical-medical hospital-clinic 40, provider group 42 can connect and communicate with affiliated hospital-clinics 60 for additional patient-care expertise, as required. Goal: provide maximal patient care quality, as a stand-alone entity.

That communications connection—a wide-area network of global reach—is managed by an information-technology system for communications and computing 50. There is a system 50 at surgical-medical hospital-clinic 40 and a system 50 at supporting hospital-clinic 60. Then the two systems 50 are connected via network linkages 62 which allow two-way video-voice-Internet-FAX/imaging consultations on patient care. To ensure maximal quality, the connection is redundant and route-diverse, to prevent service interruptions at a life-or-death moment. Depending on the existing network-system architecture, the connections can wireless, wireline, or wireless/wireline.

Following treatment and discharge, patients 10 can either ask to be transported 30 home, stay in the area to visit, or use their personal transport choice to return home.

CONCLUSION, RAMIFICATION AND SCOPE

As illustrated, the reader will see that my invention improves over the prior art by offering the millions of Americans considering "medical tourism" a less-polluting,[1] safer, and family-friendly choice for specialty care surgical-medical treatment. Rather than flying up to 16,000 miles to an exotic location, they and their loved ones can stay close in a safe environment, with rule of law a priority.

[1] approximately up to 6,000 pounds of $CO^2$ less per patient

My invention empowers them by offering them more choices for treatment, rather than the "take-it-or-leave-it" attitude reported in many areas across the U.S. Further, my invention has the following advantages over the prior art:

- it boosts job development and economic development in areas that the residents believe have been ignored and neglected for decades;
- it increases collaboration between patients, American Indian/Alaskan Native tribal nations, U.S. government, state and local governments, and the global community;
1. it provides another solution to the Medicaid/Medicare funding crises.
- it challenges existing providers—now facing the prospect of patients who have another treatment option—to reconsider how appropriately they are meeting patient needs ("raises the performance bar");
- it provides a "clean-sheet/green-field/blue-ocean" opportunity to implement best-practices in health care without past issues encumbering the highest quality patient care possible;
- it creates new medical knowledge for the world; and
- it provides the Indian Health Service of the U.S. with another choice of vendor for specialty care surgical-medical treatments. Given IHS is 100%-separate from present invention and working in significantly-different functional areas.

Although the illustrated embodiment contains many specifics, they should not be construed as limiting the scope of my invention. Rather, the illustrated embodiment is providing an illustration of one embodiment.

EXAMPLE

There are more than 520 federally-recognized American Indian/Alaskan Native tribal-nations. In theory, any one of them could host a hospital-clinic 40. Further, the novel, non-obvious knowledge in my invention could be applied as gaming-as-economic development has been applied.

Thus, the scope of my invention should be determined by the appended claims and their legal equivalents. rather than the example given. The goal: saving lives by preventing needless delays due to high costs.

I claim:

1. A system for treating medical patients, the system comprising:
    a medical hospital located within the Mandan Indian tribal nation lands in the state of North Dakota recognized by the United States of America federal government,
        wherein said Mandan Indian tribal nation establishes, under the tribal nation's sovereign authority, the requirements for the delivery of a plurality of treatment services to said medical patients and the requirements for adjudication of medical malpractice claims; and
    wherein said hospital is one of fixed construction and a mobile unit;
    wherein said hospital is within 120 miles of an airfield capable of handling 150 passenger jet airplanes; and
    wherein said hospital is accredited by the Joint Commission International; and
    wherein said hospital provides said plurality of treatment services including: colon, rectal and vascular surgery services, plastic surgery services, thoracic cardiovascular and urologic surgery services, surgery services of the hand, and neurologic, ophthalmologic, oral, maxillofacial, orthopaedic and otolaryngology treatment services,
    wherein said hospital is configured to be staffed by a plurality of medical providers, under contract with the hospital to provide said treatment services, and to provide administration, patient management, human resources and provisioning, wherein said medical providers are citizens of Thailand; and
    wherein said medical patients are not American Indians or Alaskan Natives; and
    wherein said medical patients are transported to and from said airfield by passenger buses; and
    an information technology sub-system within said hospital configured to provide computing and communications; including: an apparatus of wide-area network linkages, configured to provide communications with affiliated hospitals, clinics and medical colleges, including for consulting about patient treatment including two-way video, voice and imaging consultations, Internet connectivity and fax capability.

* * * * *